United States Patent [19]

Janicke et al.

[11] Patent Number: 4,753,954
[45] Date of Patent: Jun. 28, 1988

[54] FUNGICIDAL COMPOSITIONS AND METHODS OF COMBATTING FUNGI EMPLOYING A SYNERGISTIC COMBINATION OF PROPICONAZOL AND FENPROPIDIN

[75] Inventors: Reinhard Janicke; Robert Nyfeler, both of Basel, Switzerland

[73] Assignee: Ciba-Geigy Corporation, Ardsley, N.Y.

[21] Appl. No.: 12,534

[22] Filed: Feb. 9, 1987

[30] Foreign Application Priority Data

Feb. 14, 1986 [CH] Switzerland .................... 595/86

[51] Int. Cl.⁴ ...................... A01N 43/40; A01N 43/64
[52] U.S. Cl. ..................................... 514/317; 514/383
[58] Field of Search ............................. 514/317, 383

[56] References Cited

U.S. PATENT DOCUMENTS

| | | | |
|---|---|---|---|
| 4,079,062 | 3/1978 | Van Reet | 71/92 |
| 4,202,894 | 5/1980 | Pfiffner | 514/227 |
| 4,241,058 | 12/1980 | Pfiffner | 546/153 |

FOREIGN PATENT DOCUMENTS

| | | |
|---|---|---|
| 48997 | 4/1982 | European Pat. Off. . |
| 1522657 | 8/1978 | United Kingdom . |

OTHER PUBLICATIONS

Research Disclosure No. 26402 (Apr. 1986).

*Primary Examiner*—Allen J. Robinson
*Attorney, Agent, or Firm*—Edward McC. Roberts; Meredith C. Findlay

[57] ABSTRACT

Combinations of the fungicides propiconazol and fenpropidin, which are both inhibitors of ergosterol biosynthesis, exhibit a synergistically enhanced activity against fungi. The active components may also be applied individually in immediate succession.

4 Claims, No Drawings

FUNGICIDAL COMPOSITIONS AND METHODS OF COMBATTING FUNGI EMPLOYING A SYNERGISTIC COMBINATION OF PROPICONAZOL AND FENPROPIDIN

The present invention relates to fungicidal compositions with synergistically enhanced activity against fungi and to a method of using such compositions.

The compositions of the present invention are based on two active components which have both become known as inhibitors of ergosterol synthesis but which belong to two different chemical classes.

Component I is the fungicide propiconazol, namely 1-[2-(2,4-dichlorophenyl)-4-propyl-1,3-dioxolan-2-ylmethyl]-1H-1,2,4-triazole of the formula

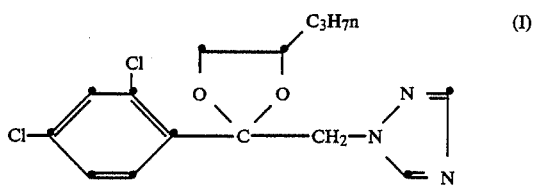

or a salt thereof. Said fungicide is described in GB 1,522,657.

Component II is the fungicide fenpropidin, namely 1-[3-(4-tert-butylphenyl)-2-methylpropyl]piperidine of the formula

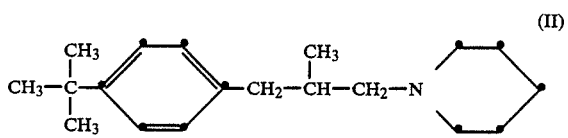

or a salt thereof. Said fungicide is described in German Offenlegungsschrift No. 27 52 135.

Propiconazol (component I) may occur in four stereoisomeric forms which differ in their fungicidal activity. Fenpropidin (component II) occurs in two enantiomeric forms which also differ in their fungicidal activity. It is a further aspect of the invention that it comprises mixtures of pure isomers I and II.

Examples of acids which can be used for the preparation of salts of formula I or II are: hydrohalic acids such as hydrofluoric acid, hydrochloric acid, hydrobromic acid or hydriodic acid, as well as sulfuric acid, phosphoric acid, nitric acid and organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

The term "salts" also comprises metal complexes of the two basic components I and II. In the compositions of the invention, either one component or both components independently may be present in the form of a salt. Metal complexes in which both components I and II are combined to form a mixed complex may also be prepared.

Metal complexes consist of the fundamental organic molecule and an inorganic or organic metal salt. Examples of such metal salts are the halides, nitrates, sulfates, phosphates, acetates, trifluoroacetates, trichloroacetates, propionates, tartrates, sulfonates, salicylates, benzoates, etc. of elements of the second main group, e.g. calcium and magnesium, and of the third and fourth main groups, e.g. aluminium, tin or lead, and also of the first to eighth subgroups, e.g. chromium, manganese, iron, cobalt, nickel, copper, zinc etc. The subgroup elements of the 4th period are prefrred. The metals may be present in any of the valencies attributed to them. The metal complexes may be mono- or polynuclear, i.e. they may contain one or more molecular components as ligands, e.g. as is the case with the above-mentioned mixed complexes of propiconazol and fenpropidin.

In practice, it is advantageous to employ components I and II in pure form, to which components further agrochemical active substances such as insecticides, acaricides, nematicides, herbicides, growth regulators, fertilisers and, in particular, other microbicides may also be added.

It is known to the skilled person that the fungicidal activity of a substance can usually be broadened by the addition of a second fungicide which has a different direction of action. The skilled person will combine two active substances which are chemically compatible with each other and which, conveniently, act as fungicides by virtue of different biological mechanisms. Thus, for example, GB patent application No. 2,110,934 describes fungicidal compositions in which one component is an inhibitor of adenosine desaminase and the other is an inhibitor of ergosterol biosynthesis (in the cell membrane of the fungus). In GB patent application No. 2,110,934, in addition to other substance types, both triazole derivatives and piperidine derivatives are cited as being ergosterol inhibitors.

Surprisingly, it has been found that the two fungicides propiconazol and fenpropidin which have become known and which belong to the same group of inhibitors of ergosterol biosynthesis exhibit an immensely enhanced activity when employed in admixture or in immediate succession. Not only is this activity superior to that of the individual components, it is also distinctly greater than additive, i.e. synergistic.

Moreover, pathogens with a diminished sensitivity to fungicides from the class of triazoles can also be fully controlled with such a combination of active ingredients.

Hence the present invention constitutes a substantial enrichment of the state of the art.

The present invention relates not only to the two-component composition but also to a method of controlling fungi which comprises treating a locus which is already infected by fungi, or is liable to be infected, in any order or simultaneously, with (a) the active component propiconazol of formula I or a salt thereof and with (b) the active component fenpropidin of formula II or a salt thereof, which salts may be selected such that both active components are attached to one acid radical or, in the case of a metal complex, both components are attached to a central metal cation.

Favourable ratios of the two active components are: I:II=20:1 to 1:20, in particular 10:1 to 1:20, preferably I:II=5:1 to 1:5. In many cases advantageous combinations are those in which the ratio of the pure active components is: I:II=1:1 to 1:5, in particular 3:2 to 1:3, e.g. 2:5.

The combinations of active components I+II of this invention have very useful curative, preventive and systemic fungicidal properties for protecting cultivated plants. With these combinations it is possible to inhibit or destroy the microorganisms which occur in plants or parts of plants (fruit, blossoms, leaves, stems, tubers, roots) in different crops of useful plants, while at the same time the parts of plants which grow later are also protected from attack by such microorganisms. This also applies in particular to microorganisms that have developed slight resistance to fungicides of the triazole class.

The combinations are effective against the phytopathogenic fungi belonging to the following classes: Ascomycetes (e.g. Venturia, Podosphaera, Erysiphe, Monilinia, Uncinula); Basidiomycetes (e.g. the genera Hemileia, Rhizoctonia, Puccinia); *Fungi imperfecti* (e.g. Botrytis, Helminthosporium, Rhynchosporium, Fusarium, Septoria, Cercospora, Alternaria and, especially, Pyricularia). In addition, the combinations have a systemic action. They can also be used as seed dressing agents for protecting seeds (fruit, tubers, grains) and plant cuttings against fungus infections as well as against phytopathogenic fungi which occur in the soil. The combinations of the invention are especially well tolerated by plants and they are ecologically non-harmful.

Without implying any limitation, target crops to be protected within the scope of the present invention comprise e.g. the following species of plants: cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconuts, castor oil plants, cocoa beans, groundnuts), cucumber plants (cucumber, marrows, melons) fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers).

The combinations of the active components of formulae I and II are normally applied in the form of compositions. The active components of formula I and II can be applied simultaneously to the crop area or plant to be treated, or they may be applied in succession within 24 hours, if desired together with further carriers, surfactants or application promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a combination comprising at least one active component of formula I and one active component of formula II is application to the parts of plants above the soil, especially the leaves (foliar application). The number of applications and the rate of application depend on the biological and climatic life conditions of the pathogen. However, the active components can also penetrate the plant through the roots via the soil (systemic action) by drenching the locus of the plant with a liquid formulation, or by applying the components in solid form to the soil, e.g. in granular form (soil application). The active components of formulae I and II may also be applied to seeds (coating) either by impregnating the seeds with a liquid formulation of one component and then with a liquid formulation of the other component or by coating them with a combined formulation. In special cases, further types of application are also possible, e.g. selective treatment of the buds or fruit.

The components of the combination are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing cirumstances. Advantageous rates of application are normally from 50 g to 2 kg a.i./ha, most preferably from 100 g ot 600 g a.i./ha.

The formulations are prepared in known manner, e.g. by homogeneously mixing and/or grinding the active components with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverised plant residues. Particularly advantageous application promoting adjuvants which are able to reduce substantially the rate of application are also natural (animal or vegetable) or synthetic phospholipids of the series of the cephalins and lecithins, e.g. phosphatidyl ethanolamine, phosphatidyl serine, phosphatidyl glycerol, lysolecithin, plasmalogenes or cardiolipin, which can be obtained e.g. from animal or plant cells, in particular from the brain, heart, liver, egg yokes or soya beans. Examples of useful physical forms are phosphatidyl choline mixtures. Examples of synthetic phospholipids are dioctanoylphosphatidyl choline and dipalmitoylphospatidyl choline.

Depending on the nature of the active components of formulae I and II to be formulated, suitable surface-active compounds are non-ionic, cationic and/or anionic surfactants having good emulsifying, dispersing and wetting properties. The term "surfactants" will also be understood as comprising mixtures of surfactants.

In the following Formulation Examples, the term "active ingredient" will be understood as meaning a combination of components I and II in the ratio 3:2 to 1:3 (throughout, percentages are by weight).

| Wettable powders | (a) | (b) | (c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants, and the mixture is thoroughly ground in a suitable mill, affording wettable powders which can be diluted with water to give suspensions of the desired concentration.

| Emulsifiable concentrate | |
|---|---|
| active ingredient | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
|---|---|---|
| active ingredient | 5% | 8% |
| talcum | 95% | — |
| kaolin | — | 92% |

Ready-for-use dusts are obtained by mixing the active ingredient with the carriers, and grinding the mixture in a suitable mill.

| Extruder granulate | |
|---|---|
| active ingredient | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Coated granulate | |
|---|---|
| active ingredient | 3% |
| polyethylene glycol 200 (mol wt.) | 3% |
| kaolin | 94% |

The finely ground active ingredient is uniformly applied, in a mixer, to the kaolin moistened with polyethylene glycol. Non-dusty coated granulates are obtained in this manner.

A synergistic effect has been achieved with fungicides if the fungicidal action of the combination of active components is greater than the sum of the action of the individually applied components.

The expected action E for a given combination of active components, e.g. of two fungicides, can be calculated in accordance with the so-called COLBY formula [originally only used to calculate the expected value E of combinations of herbicides]:

$$E = X + Y - \frac{X \cdot Y}{100}$$

wherein

X = action (in %) of fungicide I at p g a.i./ha
Y = action (in %) of fungicide II at q g a.i./ha
E = expected action of fungicides I+II at p+q g a.i./ha
[(1) COLBY, L. R. "Calculating synergistic and antagonistic responses of herbicide combinations", Weeds 15, pp. 20–22. (2) LIMPEL et al., 1062 "Weeds control by . . . certain combinations". Proc. NEWCL. Vol. 16, pp. 48–53.]

If the actually observed value (O) is higher than the expected value (E), then the action of the combination is greater than additive, i.e. then there is synergism.

In the following Example, E was calculated in accordance with the above equation.

FUNGICIDAL ACTION AGAINST POWDERY MILDEW ON WINTER WHEAT 95 winter wheat plants of the "Kanzler" variety are reared in 11 cm deep seed dishes (base: 30×40 cm) in a greenhouse at 20° C. When the plants have reached the 2-leaf stage, they are inoculated with an isolate of Erysiphe graminis tritici which is completely sensitive to DMI fungicides.

When fungus attack becomes visible 5 days after inoculation (3-leaf stage; 10–12% attack), an aqueous suspension of the individual fungicide or of the combination of fungicides is applied with a spray device under field conditions. After application, evaluation is made, at regular intervals, of the extent of fungus attack on those leaves which were on the plants at the moment of inoculation (evaluation of primary infestation) as compared with untreated control plants.

The rates of application indicated in the Table are employed. 3 replicates of each partial assay are carried out. In the following, evaluation is made after 22 days.

TABLE

| Partial assay No. | g a.i./ha Component I | g a.i./ha Component II | Fungus attack (in %) | E Action (%) calculated [COLBY] | O Action (%) found |
|---|---|---|---|---|---|
| 1 (control) | — | — | 100 | — | — |
| 2 | 10 | — | 97 | — | 3 |
| 3 | 30 | — | 47 | — | 53 |
| 4 | 50 | — | 16 | — | 84 |
| 5 | — | 10 | 95 | — | 5 |
| 6 | — | 30 | 87 | — | 13 |
| 7 | — | 50 | 63 | — | 37 |
| 8 | 10 | 10 | 83 | 12 | 17 |
| 9 | 10 | 30 | 63 | 19 | 37 |
| 10 | 10 | 50 | 22 | 41 | 78 |
| 11 | 30 | 10 | 37 | 55 | 63 |
| 12 | 30 | 30 | 16 | 59 | 84 |
| 13 | 30 | 50 | 4 | 70 | 96 |
| 14 | 50 | 10 | 7 | 85 | 93 |
| 15 | 50 | 30 | 9 | 86 | 91 |

TABLE-continued

| | Evaluation 22 days after application | | | | |
|---|---|---|---|---|---|
| | g a.i./ha | | Fungus | E Action (%) | O Action |
| Partial assay No. | Component I | Component II | attack (in %) | calculated [COLBY] | (%) found |
| 16 | 50 | 50 | 2 | 90 | 98 |

As can be seen from the Table, in partial assays 9 to 16 combinations of components I and II in a wide variety of ratios exhibit an enhanced synergistic activity.

Similar enhanced synergistic activity is also exhibited against barley mildew, barley rust (Puccinia spp.) and other pathogens.

What is claimed is:

1. A method of controlling fungi, which method comprises treating a locus which is already infected by fungi, or is liable to be infected, in any order or simultaneously, with (a) the active component propiconazol of formula I

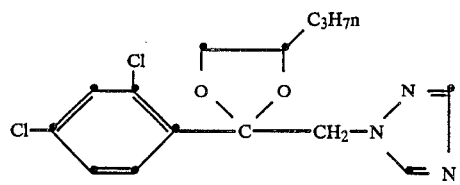

or a salt thereof, and with (b) the active component fenpropidin of formula II

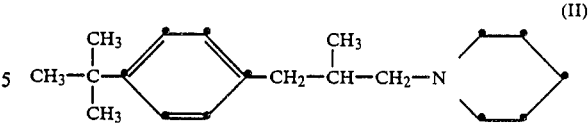

or a salt thereof, the amount of each applied so that the weight ratio of I:II is 5:1 to 1:5, the amounts of the two components being selected so that the total mixture ultimately applied to the locus is effective to control said fungi.

2. A fungicidal composition comprising at least two active components, one of which is propiconazol of formula I, or a salt thereof,

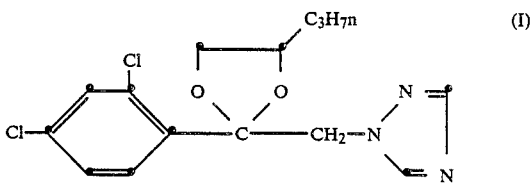

and the other is fenpropidin of formula II

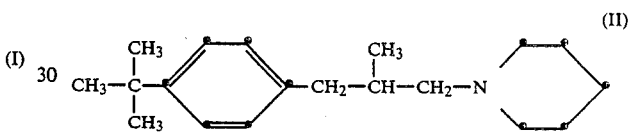

wherein the weight ratio of I:II is 5:1 to 1:5.

3. A composition according to claim 2, wherein the weight ratio of I:II is 3:2 to 1:3.

4. A composition according to claim 2, wherein the weight ratio of I:II is 1:1 to 1:5.

* * * * *